Figure 1A:
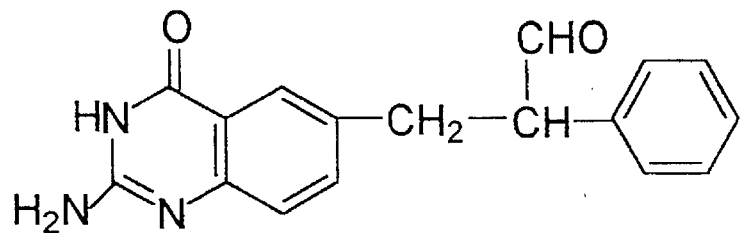
Figure 1A:
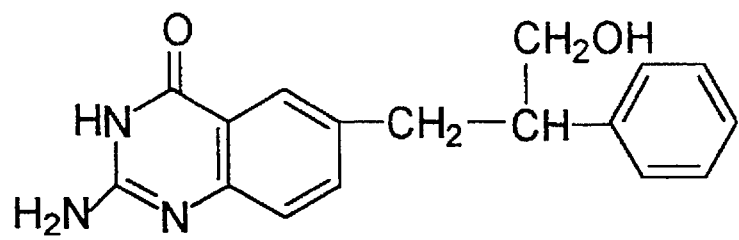
Figure 1A:
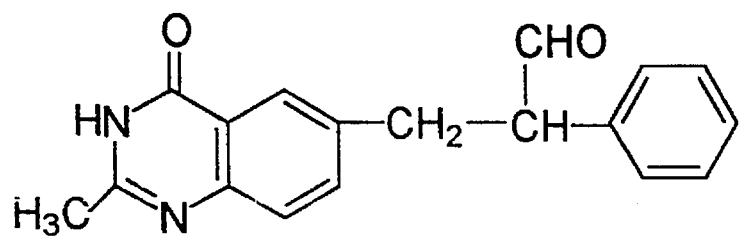
Figure 1A:
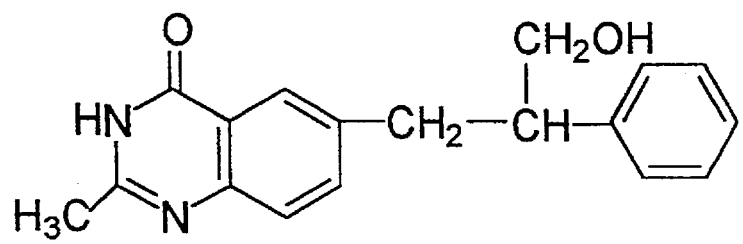

United States Patent [19]
Nair et al.

[11] Patent Number: 5,593,999
[45] Date of Patent: Jan. 14, 1997

[54] NON-CLASSICAL FOLATE ANALOGUE INHIBITORS OF GLYCINAMIDE RIBONUCLEOTIDE FORMYLTRANSFERASE (GARFT)

[76] Inventors: Madhavan G. Nair, 7005 Charleston Oaks Dr. N., Mobile, Ala. 36695; Li Liu, 207 Hillcrest Rd. Apt #118, Mobile, Ala. 36608

[21] Appl. No.: 480,814

[22] Filed: Jun. 7, 1995

[51] Int. Cl.$^6$ ............ C07D 401/06; C07D 409/06; C07D 405/06; C07D 239/90
[52] U.S. Cl. ............ 514/260; 544/284; 544/287
[58] Field of Search ............ 544/287, 284; 514/260

[56] References Cited

U.S. PATENT DOCUMENTS

| | | | |
|---|---|---|---|
| 4,447,608 | 5/1984 | Jones et al. | 544/287 |
| 4,889,859 | 12/1989 | Taylor et al. | 514/258 |
| 5,081,124 | 1/1992 | Hughes | 514/259 |
| 5,145,854 | 9/1992 | Nair et al. | 514/259 |
| 5,430,148 | 7/1995 | Webber et al. | 544/238 |

OTHER PUBLICATIONS

Nair et al. "Synthesis of the reduced derivatives of 11–deazahomofolic acid . . . inhibitors of GARFT" J. Med. Chem. 32, 1277 (1989) month of publication not provided.
Nair et al. Inhibitors of glycinamide ribonucleotide formyltransferase GARFT. Drugs of the Future. 18(4):335–342 (1993) month of publication not provided.

*Primary Examiner*—Mukund J. Shah
*Assistant Examiner*—King Lit Wong

[57] ABSTRACT

Several new 10-formyl and 10-hydroxymethyl derivatives of 5,8,10-trideazapteroic acid are provided, as well as procedures for their preparation. These compounds were shown to be powerful inhibitors of glycinamide ribonucleotide formyltransferase (GARFT), an enzyme that mediates the de novo biosynthesis of purine nucleotides that are required for DNA synthesis and cell division. Due to their ability to interfere with nucleotide biosynthesis and to penetrate microbial cells they are potential anti-microbial agents and are useful for the treatment of opportunistic infections in AIDS and other infections caused by micro-organisms that are resistant to conventional anti-bacterial and anti-fungal agents.

25 Claims, 5 Drawing Sheets

Scheme 1
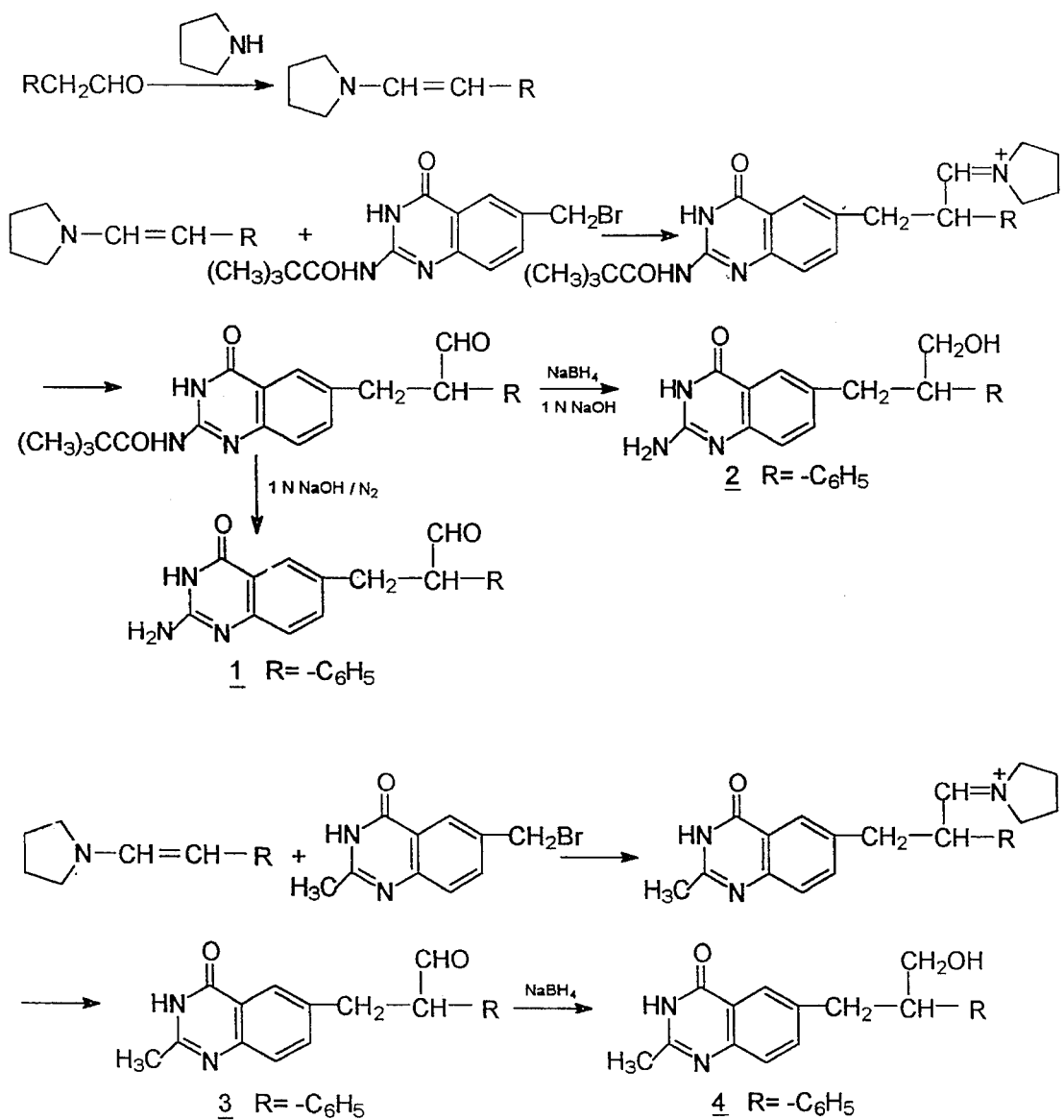

1

2

3

4

Figure 1B

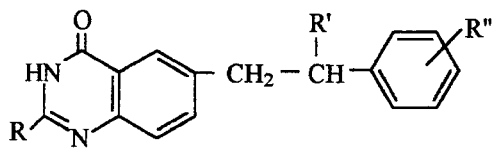

5 (a-l): R = -NH$_2$; R' = -CHO; R" = -F; -CF$_3$; -NO$_2$; -NH$_2$; -Cl; -Br; -COOCH$_3$;
-CH$_3$; -OCH$_3$; -OH; -C$_6$H$_5$; -OC$_6$H$_5$.

6(a-l): R = -CH$_3$; R' = -CHO; R" = -F; -CF$_3$; -NO$_2$; -NH$_2$; -Cl; -Br; -COOCH$_3$;
-CH$_3$; -OCH$_3$; -OH; -C$_6$H$_5$; -OC$_6$H$_5$.

7 (a-l): R = -NH$_2$; R' = -CH$_2$OH; R" = -F; -CF$_3$; -NO$_2$; -NH$_2$; -Cl; -Br; -COOCH$_3$;
-CH$_3$; -OCH$_3$; -OH; -C$_6$H$_5$; -OC$_6$H$_5$.

8 (a-l): R = -CH$_3$; R' = -CH$_2$OH; R" = -F; -CF$_3$; -NO$_2$; -NH$_2$; -Cl; -Br; -COOCH$_3$;
-CH$_3$; -OCH$_3$; -OH; -C$_6$H$_5$; -OC$_6$H$_5$.

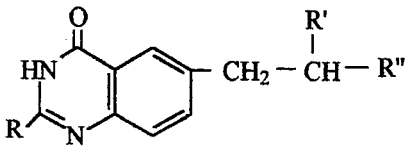

9(a-e): R = -NH$_2$; R' = -CHO; R" = pyridyl; naphthyl; thienyl; furanyl; quinolyl.

10(a-e): R = -CH$_3$; R' = -CHO; R" = pyridyl; naphthyl; thienyl; furanyl; quinolyl.

11(a-e): R = -NH$_2$; R' = -CH$_2$OH; R" = pyridyl; naphthyl; thienyl; furanyl; quinolyl.

12(a-e): R = -CH$_3$; R' = -CH$_2$OH; R" = pyridyl; naphthyl; thienyl; furanyl; quinolyl.

Scheme 2
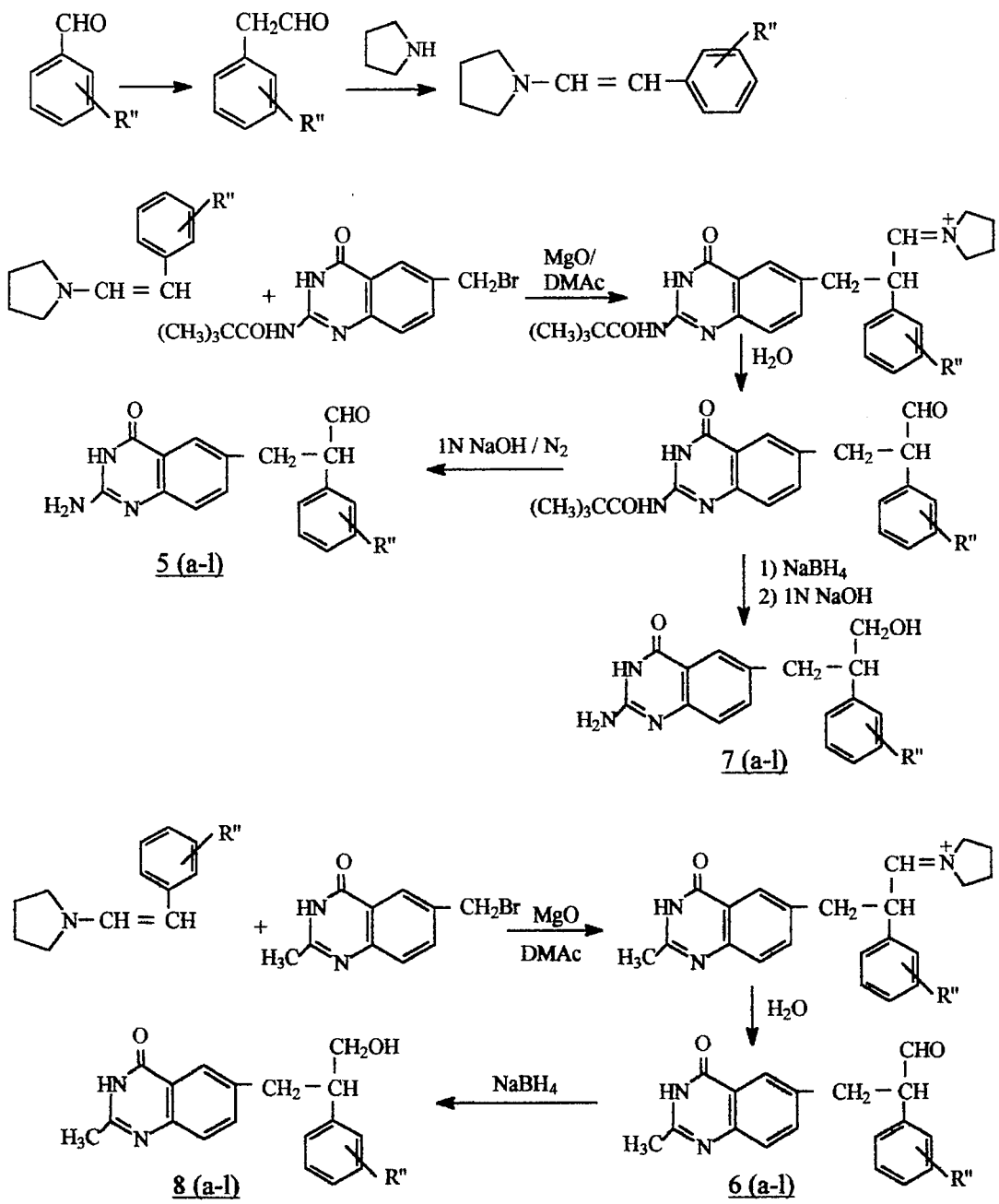

Scheme 3
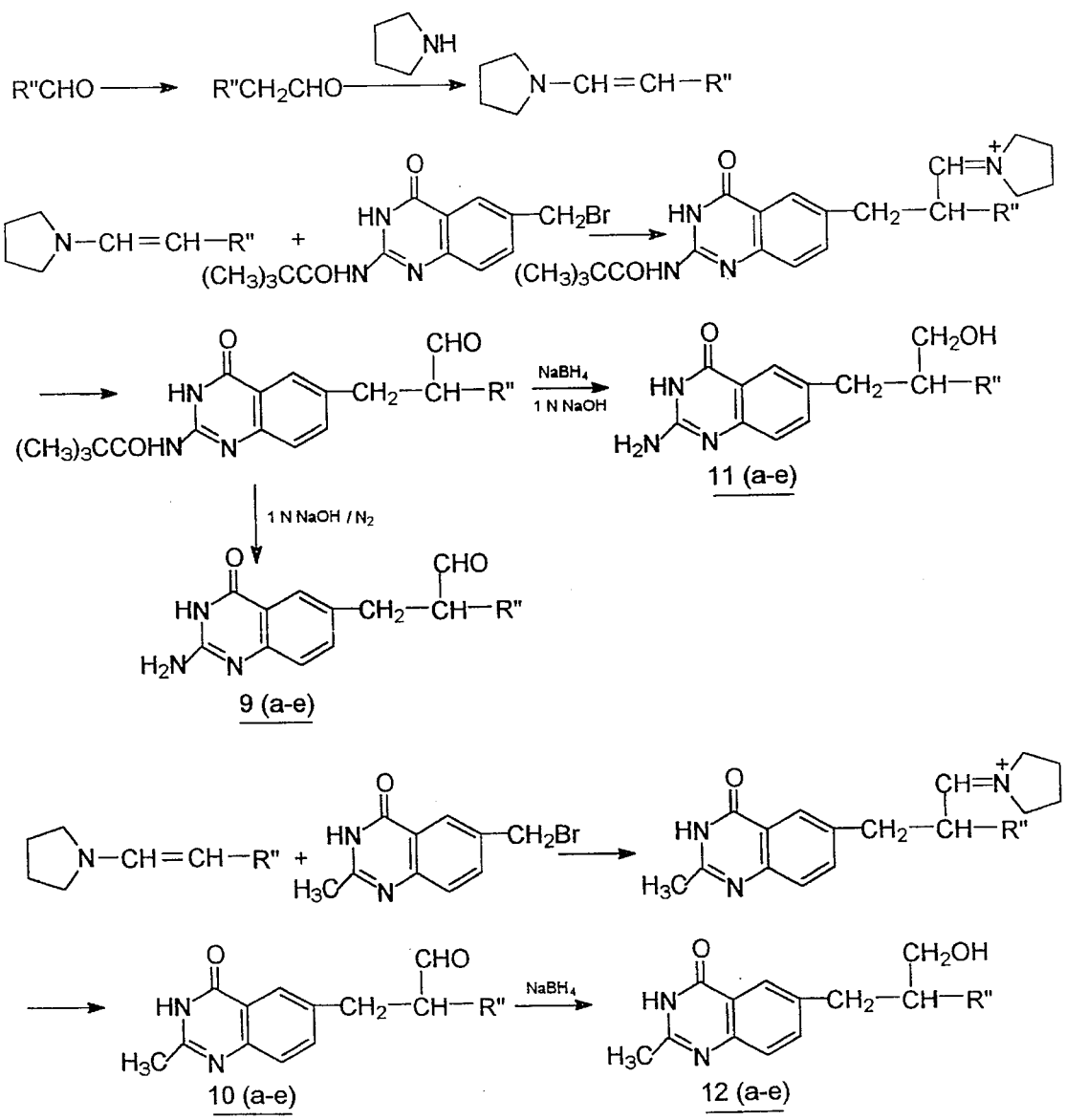

NON-CLASSICAL FOLATE ANALOGUE INHIBITORS OF GLYCINAMIDE RIBONUCLEOTIDE FORMYLTRANSFERASE (GARFT)

FIELD OF INVENTION

This invention relates to the use of inhibitors of the enzyme glycinamide ribonucleotide formyltransferase (GARFT) as antimicrobial agents. These entities are hitherto undescribed non-classical folate antagonists.

The process of this invention is illustrated by the reaction sequence depicted in Schemes 1, 2 and 3, where the compound numbers identify the same compounds which they identify in all descriptions.

USE ADVANTAGE

*Pneumocystis carinii* (*P. carinii*) is an organism originally thought to be a protozoan but reclassified as a fungus (J. C. Edman; J. A. Kovacs; H. Masur; D. V. Santi et al. Nature, 334,519,1988). *Toxoplasma gondii* (*T. gondii*) is a coccidian protozoan. Both of them are opportunistic pathogens of immunocompromised hosts especially patients infected with the AIDS virus. According to one estimate up to 85% of patients with AIDS will develop *Pneumocystis carinii* pneumonia (PCP) during the course of their disease. As many as 60,000 patients annually may develop PCP in the United State. Toxoplasmosis has also emerged as a leading opportunistic infection associated with AIDS (F. G. Araujo; D. G. Guptill and J. S. Remington. J. Infect. Dis. 156, 828, 1987.). These two opportunistic infections cause significant morbidity and mortality in patients with AIDS.

The most commonly used drugs for the treatment of *P. carinii* and *T. gondii* infections are dihydrofolate reductase (DHFR) inhibitors such as trimethoprim (TMP), pirimethamine and trimetrexate (F. R. Scattler and J. Feinberg. Chest, 101,451,1992; G. W. Amsden, S. F. Kowalsky and G. D. Morse. The Annals of Pharmacology, 26, 218, 1992). TMP and pirimethamine are weaker inhibitors of *P. carinii* and *T. gondii* DHFR and they are used in combination with sulfamethoxazole. Although trimetrexate is a very potent inhibitor of *P. carinii* and *T. gondii* DHFR, it is more inhibitory towards the mammalian enzyme. Thus, patients treated with these agents require concomitant leucovorin administration to avoid unacceptable toxicity. (C. J. Allegra, J. A. Kovacs, J. C. Drake et al. J. Exp. Med. 165,926,1987); F. R. Sattler and C. J. Allegra. J. Infect. Dis. 161, 91,1990.). The toxicity of these drugs remains a potential problem even with the co-administration of leucovorin.

Antimicrobial agents that are targeted to the folate dependent enzyme glycinamide ribonucleotide formyltransferase (GARFT) will have potential use as treatments for microbial infections that are unresponsive to conventional DHFR inhibitors. These compounds will also be more specific and less toxic than dihydrofolate reductase (DHFR) inhibitors, that cause a general blockade of one-carbon metabolism.

The specific compounds described herein are non-classical analogues of 10-formyl-5,8,10-trideazafolate (FTDF) which has been shown to be a potent inhibitor of mammalian GARFT. They posses the 10-formyl-10-deazafolate pharmacophore for GARFT inhibition. Structural modifications are carried out at the benzene ring region to improve transport of these compounds to micro-organisms, solubility and other features to enhance selectivity of inhibition towards the microbial enzymes. The new entities differ from FTDF both in chemical structure and biological properties. FTDF and other classical folate antagonists are unable to penetrate microbial cells due to their need for the reduced folate transporter (RFT) for influx. The non-classical folate antagonists described herein are able to enter microbial cell by facilitated diffusion and cause preferential inhibition of microbial GARFT relative to the mammalian enzyme. Therefore, the compounds provided herein should have clinical utility as novel anti-microbial agents. In addition they are expected to be useful in the treatment of microbial infections that are resistant to conventional antifolate antibiotics.

This invention accordingly also provides a process for treating microbial infections which comprises administering to a warm-blooded animal having such infections a therapeutic non-toxic amount of compounds 1, 2, 3, 4, and their close analogues that are represented in FIG. 1b, in the form of a pharmacologically acceptable formulation thereof.

The process of the invention for the preparation of compounds 1–4, and their close analogues are depicted in schemes 1, 2 and 3.

Briefly, appropriate aldehydes were homologated by reaction with methoxymethylene phosphonium chloride in a typical Wittig reaction. The homologated aldehydes were then converted into their corresponding enamines by reaction with pyrrolidine. The resulting enamine derives of the aldehydes were subsequently reacted with 4(3H)-oxo-6-(bromomethyl)-2-methyl quinazoline or 2-pivaloylamino-4(3H)-oxo-6-(bromomethyl) quinazoline in the presence of MgO in DMAc to directly generate the 10-deaza-10-formyl compounds. The pivaloyl protective group of the respective pivaloyl compounds was removed by treatment with 1N NaOH in MeOH at room temperature under $N_2$ to produce the target compounds The 10-deaza-10-hydroxymethyl compounds were obtained by reaction of the respective 10-deaza-10-formyl compounds with sodium borohydride in methanol. Alternately the 10-deaza-10-formyl compounds may be converted to the 10-deaza-10-hydroxymethyl compounds by $NaBH_4$ reduction and the subsequent deprotection of pivaloyl group. The required quinazoline starting materials were prepared according to our previously reported procedures.

The 10-formyl-5,8,10-trideazapteroate compounds or the 10-hydroxymethyl-5,8,10-trideazapteroate compounds can be administered to a warm blooded animal as such or in association with a pharmaceutically acceptable diluent or carrier to treat microbial infections (bacterial, fungal and protozoan), neoplastic diseases, or autoimmune diseases such as rheumatoid arthritis. The carrier or diluent can be solid, semi-solid or liquid and can serve as a vehicle, excipient or medium for the compounds. Examples of diluent and carriers include but not limited to lactose, dextrose, mannitol, sucrose, sorbitol, gum acacia, starch, calcium phosphate, mineral oil, oil of theobroma, gelatin, methyl cellulose, talc, magnesium stearate, alginates, polyethylene glycol etc. The 10-formyl or 10-hydroxymethyl-5,8,10-trideazapteroate compounds and carrier or diluent can be enclosed or encapsulated in a capsule, sachet, cachet, gelatin, paper or other container and can take the form of tablets, capsules, cachets or suppositories.

The 10-formyl or 10-hydroxymethyl-5,8,10-trideazapteroate compounds as such or with a carrier or diluent can be administered to a warm-blooded animal having microbial infections, or evidence of neoplastic or autoimmune diseases by an available route including oral and parenteral (intravenous, intraperitoneal, subcutaneous, and intra-muscular) administration.

The invention accordingly also provides a pharmaceutical composition in dosage unit form comprising from 1.0 to about 750 mg of 10-formyl or 10-hydroxymethyl-5,8,10-trideazapteroate compound per dosage unit as such or together with a pharmaceutically acceptable non-toxic carrier or diluent thereof. The total amount administered to treat microbial infections, neoplastic or auto-immune diseases is that imposed by toxic side effects and can be determined by trial and error for the animal to be treated including normally administered in conjunction with leucovorin (d,1-5-formyltetrahydrofolate) to reduce toxicity.

Representative 10-deaza-10-formyl and 10-deaza-10-hydroxymethyl pteroate analogues were evaluated as inhibitors of *L. casei* glycinamide ribonucleotide formyltransferase and their inhibitory activity compared to the well-known GARFT inhibitor 5,10-didezatetrahyddrofolate (DDATHF) under identical experimental conditions.

2-Amino-6-($2^1$-formyl-$2^1$-phenyl ethyl)-4(3h)-oxoquanazoline (1) and 2-amino-6-($2^1$-hydroxymethyl-$2^1$-phenyl ethyl)-4 (3H)-oxoquanazoline (2) exhibited $I_{50}$ values for *L. casei* GARFT at $8 \times 10^{-6}$M and $2.7 \times 10^{-4}$M respectively. Methyl 10-formyl-5,8,10-trideazapteroate (5 g) also exhibited powerful inhibition of *L. casei* GARFT with an $I_{50}$ value of $7.0 \times 10^{-6}$M. DDATHF under identical conditions, exhibited an $I_{50}$ value of $2.3 \times 10^{-6}$M. Since the nonclassical analogs that are recited in claims 1,2,3 and 4 do not possess a glutamate moiety and lack the presence of 8-nitrogen, both previously considered to be necessary for GARFT inhibition, the present result are new novel and unexpected. The compounds recited in claims 1,2,3, and 4 and their close analogues are lipophilic and capable of penetrating microbial cells by diffusion as opposed to the classical glutamate containing folate antagonists and therefore they are useful in the treatment of a number of microbial infections, including opportunistic infections in AIDS.

In addition to the above novel structural features, and powerful enzyme inhibition, compounds processing the 10-deaza-10-formyl pharmacophore are capable of irreversibly inactivating *L. casei* GARFT in a concentration and time dependent manner. For example pre-incubation of *L. casei* GARFT with the substrate GAR and one of the 10-deaza-10-formylquinazoline compound [Example: compound(1)] for 10 minutes completely abolishes enzyme activity, that could not be restored even after adding a 300% excess of the folate cofactor 5,8-dideaza-10-formyl folic acid. These new and unexpected results substantiate that the mechanism of GARFT inhibition by 1 or 5 g differs from that of DDATHF and its analogues; thus providing additional novelty and enhanced utility for compound 1 and the analogues described herein.

EXAMPLE 1

Phenylacetaldehyde pyrrolidine enamine

To a solution of 1.3 mL (10 mmol) of phenylacetaldehyde (commercially available) and 5 mL of benzene was added 0.9 mL (11 mmol) of pyrrolidine and 4.5 g of $K_2CO_3$ power. The mixture was stirred at 60° C. for 40 min. The reaction mixture was extracted with $CH_2Cl_2$ and evaporated under reduced pressure to remove the solvents and excess pyrrolidine. Yield 99%; MS(FAB$^+$), calculated for $C_{12}H_{15}N$, 173; found, 174(MH$^+$).

6-(2'-Formyl-2'-phenyl-ethyl)-2-pivaloylamino-4(3H)-oxo-quinazoline

A mixture of 1.04 g (6 mmol) of phenylacetaldehyde pyrrolidine enamine, 2.02 g (6 mmol) of 2-pivaloylamino-4(3H)-oxo-6-(bromomethyl)-quinazoline, and 360 mg (9 mmol) of MgO was stirred at 70° C. in 8 mL of DMAc for 3 hrs, during which time all the starting material had been consumed, as evidenced by TLC. The reaction mixture was extracted with 150 mL of $CH_2Cl_2$. The organic layer was washed repeatedly with water. After drying with anhydrous $Na_2SO_4$, the $CH_2Cl_2$ extract was evaporated to a small volume. The crude reaction mixture was chromatographed on a column made of silica gel in $CH_2Cl_2$. Elution of the column with 1% MeOH/$CH_2Cl_2$ and evaporation of the desired fractions (TLC) gave a yellow gum: Yield 1.4 g (61.2%); MS(FAB$^+$), calculated for $CH_{22}H_{23}O_3N_3$, 377; found, 378 (MH$^+$).

6-(2'-Formyl-2'-phenyl-ethyl)-2-amino-4(3H)-oxo-quinazoline (1)

To a solution of 0.4 g (1.06 mmol) of 6-(2'-formyl-2'-phenyl-ethyl)-2-pivaloylamino-4(3H)-oxo-quinazoline in 10 mL of MeOH at room temperature (25° C.) was added under $N_2$ 1.5 mL of 1.0N NaOH, and the mixture was stirred under $N_2$ for 16 hrs. The pH of the mixture was adjusted to 6.5 with 0.1N HCl and evaporated to 30 mL, whereupon a yellow precipitate was formed. After cooling, the precipitate was collected by filtration, washed with water, followed by a small amount of ether and $CH_2Cl_2$. Final purification of the product was carried out by column chromatography. Compound 1 was obtained as a light yellow solid; yield 250 mg (80%); mp >300° C.; MS(FAB$^+$), calculated for $C_{17}H_{15}O_2N_3$, 293; found, 294(MH$^+$).

EXAMPLE 2

Phenylacetaldehyde pyrrolidine enamine

To a solution of 1.3 mL (10 mmol) of phenylacetaldehyde (commercially available) and 5 mL of benzene was added 0.9 mL (11 mmol) of pyrrolidine and 4.5 g of $K_2CO_3$ power. The mixture was stirred at 60° C. for 40 min. The reaction mixture was extracted with $CH_2Cl_2$ and evaporated under reduced pressure to remove the solvents and excess pyrrolidine. Yield 99%; MS (FAB$^+$), calculated for $C_{12}H_{15}N$, 173; found, 174 (MH$^+$).

6-(2'-Formyl-2'-phenyl-ethyl)-2-pivaloylamino-4(3H)-oxo-quinazoline

A mixture of 1.04 g (6 mmol) of Phenylacetaldehyde pyrrolidine enamine, 2.02 g (6 mmol) of 2-pivaloylamino-4(3H)-oxo-6-(bromomethyl)-quinazoline, and 360 mg (9 mmol) of MgO was stirred at 70° C. in 8 mL of DMAc for 3 hrs, during which time all the starting material had been consumed, as evidenced by TLC. The reaction mixture was extracted with 150 mL of $CH_2Cl_2$. The organic layer was washed repeatedly with water. After drying with anhydrous $Na_2SO_4$, the $CH_2Cl_2$ extract was evaporated to small volume. The crude reaction mixture was chromatographyed on a column made of silica gel in $CH_2Cl_2$. Elution of the column with 1% MeOH/$CH_2Cl_2$ and evaporation of the desired fraction (TLC) gave a yellow gum: Yield 1.4 g (61.2%); MS(FAB$^+$), calculated for $C_{22}H_{23}O_3N_3$, 377; found, 378(MH$^+$).

6-(2'-Hydroxymethyl-2'-phenyl-ethyl)-2-amino-4(3H)-oxo-quinazoline (2)

To a solution of 1 g (2.65 mmol) of 6-(2'-formyl-2'-phenyl-ethyl)-2-amino-4(3H)-oxo-quinazoline in 20 mL of MeOH was added 113 mg (3 mmol) of NaBH$_4$ and stirred at room temperature for 4 hrs. To this reaction mixture 2 mL of 1.0N NaOH was added and stirred for another 18 hrs. The pH of the solution was adjusted to 6.5 by 1N HCl and evaporated to 2 mL. The resultant residue was triturated with 10 g of ice and the precipitate thus obtained was filtered, washed with water followed by $CH_2Cl_2$ and dried in vacuum to obtain a white solid; yield 650 mg (83%); mp 235°–237° C.; MS(FAB$^+$), calculated for $C_{17}TH_{17}O_2N_3$, 295; found, 296 (MH$^+$).

EXAMPLE 3

Phenylacetaldehyde pyrrolidine enamine

To a solution of 1.3 mL (10 mmol) of phenylacetaldehyde (commercially available) and 5 mL of benzene was added 0.9 mL (11 mmol) of pyrrolidine and 4.5 g of $K_2CO_3$ power. The mixture was stirred at 60° C. for 40 min. The reaction mixture was extracted with $CH_2Cl_2$ and evaporated under reduced pressure to remove the solvents and excess pyrrolidine. Yield 99%; MS (FAB$^+$), calculated for $C_{12}H_{15}N$, 173; found, 174(MH$^+$).

6-(2'-Formyl-2'-phenyl-ethyl)-2-desamino-2-methyl-4(3H)-oxo-quinazoline (3)

A mixture of 1.62 g (9.36 mmol) of Phenylacetaldehyde pyrrolidine enamine, 2.37 g (9.36 mmol) of 2-methyl-4(3H)-oxo-6-bromomethyl quinazoline, and 562 mg (14 mmol) of MgO was stirred at 70° C. in 15 mL of DMAc for 2.5 hrs, during which time all the starting material had been consumed, as evidenced by TLC. The reaction mixture was extracted with 300 mL of $CH_2Cl_2$. The organic layer was washed repeatedly with water. After drying with anhydrous $Na_2SO_4$, the $CH_2Cl_2$ extract was evaporated to small volume (10 ml). The crude reaction mixture was chromatographed on a column made of silica gel in $CH_2Cl_2$. Elution of the column with 2.25% MeOH/$CH_2Cl_2$ and evaporation of the desired fractions (TLC) gave pure 3 as a light yellow solid: Yield 800 mg (29.3%); mp 140°–143° C.; MS (FAB$^+$), calculated for $C_{18}H_{16}O_2N_2$, 292; found, 293 (MH$^+$).

EXAMPLE 4

Phenylacetaldehyde pyrrolidine enamine

To a solution of 1.3 mL (10 mmol) of phenylacetaldehyde (commercially available) and 5 mL of benzene was added 0.9 mL (11 mmol) of pyrrolidine and 4.5 g of $K_2CO_3$ power. The mixture was stirred at 60° C. for 40 min. The reaction mixture was extracted with $CH_2Cl_2$ and evaporated under reduced pressure to remove the solvents and excess pyrrolidine. Yield 99%; MS(FAB$^+$), calculated for $C_{12}H_{15}N$, 173; found, 174(MH$^+$).

6-(2'-Formyl-2'-phenyl-ethyl)-2-desamino-2-methyl-4(3H)-oxo-quinazoline

A mixture of 1.62 g (9.36 mmol) of Phenylacetaldehyde pyrrolidine enamine, 2.37 g (9.36 mmol) of 2-methyl-4(3H)-oxo-6-bromomethyl quinazoline, and 562 mg (14 mmol) of MgO was stirred at 70° C. in 15 mL of DMAc for 2.5 hrs, during which time all the starting material had been consumed, as evidenced by TLC. The reaction mixture was extracted with 300 mL of $CH_2Cl_2$. The organic layer was washed repeatedly with water. After drying with $Na_2SO_4$, the $CH_2Cl_2$ extract was evaporated to small volume (10 ml). The crude reaction mixture was chromatographed on a column made of silica gel in $CH_2Cl_2$. Elution of the column with 2.25% MeOH/$CH_2Cl_2$ and evaporation of the desired fractions (TLC) gave pure 3 as a light yellow solid: Yield 800 mg (29.3%); mp 140°–143° C.; MS(FAB$^+$), calculated for $C_{18}H_{16}O_2N_2$, 292; found, 293(MH$^+$).

6-(2'-Hydroxymethyl-2'-phenyl-ethyl)-2-desamino-2-methyl-4(3H)-oxoquinazoline (4)

To a stirring solution of 550 mg (1.88 mmol) of 6-(2'-formyl-2'-phenyl-ethyl)-2-desamino-2-methyl-4(3H)-oxo-quinazoline (3) in 50 mL of MeOH was added 71.2 mg (1.88 mmol) of NaBH$_4$. The reaction mixture was stirred at room temperature for 4 hrs. After adjusting the pH to 6.0 with 1.0N HCl, the reaction mixture was evaporated under reduced pressure and 10 g of ice was added. On trituration, a white solid was formed, which was filtered, washed several times with ice water followed by $CH_2Cl_2$ and dried in vacuum. Yield 300 mg (54.3%); mp 229°–232° C.; MS(FAB$^+$), calculated for $C_{18}H_{18}O_2N_2$, 294; found, 295(MH$^+$).

EXAMPLE 5g

4-Carbomethoxy phenylacetaldehyde enamine

To a solution of 10.74 g (57 mmol) of 4-carbomethoxy phenylacetaldehyde in 200 mL of benzene was added 5.14 mL (61 mmol) of pyrrolidine and 9 g of MgSO$_4$ power. The reaction mixture was stirred at 25° C. for 24 hrs and filtered. The filtrate was evaporated to 40 mL and the yellow precipitate was filtered and washed with a small amount of ether. 4-Carbomethoxy phenylacetaldehyde enamine was obtained as yellow crystal. Yield 8.0 g (60.7%); mp 131°–132° C.; MS(FAB$^+$), calculated for $C_{14}H_{17}O_2N$, 231; found, 232(MH$^+$).

6-[2'-Formyl-2'-(4-carbomethoxy phenyl)-ethyl]-2-Pivaloylamino-4(3H)-oxo-quinazoline A mixture of 3.53 g (15 mmol) of 4-carbomethoxy phenylacetaldehyde enamine, 5.07 g (15 mmol) of 2-pivaloylamino-4(3H)-oxo-6-(bromomethyl)-quinazoline, and 900 mg (22.5 mmol) of MgO was stirred at 80° C. in 25 mL of DMAc for 2.5 hrs, during which time all the starting material had been consumed, as evidenced by TLC. The reaction mixture was extracted with 150 mL of $CH_2Cl_2$. The organic layer was washed repeatedly with water. After drying with anhydrous $Na_2SO_4$, the $CH_2Cl_2$ extract was evaporated to a small volume. The crude reaction mixture was chromatographed on a column made of silica gel in $CH_2Cl_2$. Elution of the column with 1% MeOH/$CH_2Cl_2$ and evaporation of the desired fractions (TLC) gave a yellow gum: Yield 4.3 g (65.9%); MS (FAB$^+$), calculated for $C_{24}H_{25}O_5N_3$, 435; found, 436 (MH$^+$).

6-[2'-Formyl-2'-(4-carbomethoxy phenyl)-ethyl]-2-amino-4(3H)-oxoquinazoline (5g)

To a solution of 1.0 g (2.3 mmol) of 6-[2'-formyl-2'-carbomethoxy phenyl)-ethyl]-2-pivaloylamino-4(3H)-oxo-quinazoline in 35 mL of MeOH at room temperature (25° C.) was added under $N_2$ 2.5 mL of 1.0N NaOH, and the mixture was stirred under $N_2$ for 16 hrs. The pH of the mixture was adjusted to 7.0 with 0.1N HCl and evaporated to 30 mL, whereupon a yellow precipitate was formed. After cooling, the precipitate was collected by filtration, washed with water, followed by a small amount of ether and $CH_2Cl_2$. Compound 7 was obtained as a yellow solid; yield 260 mg (32.2%); mp >300° C.; MS (FAB$^+$), calculated for $C_{19}H_{17}O_4N_3$, 351; found, 352 (MH$^+$).

EXAMPLE 6g

4-Carbomethoxy phenylacetaldehyde enamine

To a solution of 10.74 g (57 mmol) of 4-carbomethoxy phenylacetaldehyde in 200 mL of benzene was added 5.14 mL (61 mmol) of pyrrolidine and 9 g of MgSO$_4$ power. The reaction mixture was stirred at 25° C. for 24 hrs and filtered. The filtrate was evaporated to 40 mL and the yellow precipitate was filtered and washed with a small amount of ether. 4-Carbomethoxy phenylacetaldehyde enamine was obtained as yellow crystal. Yield 8.0 g (60.7%); mp 131°–132° C.; MS(FAB$^+$), calculated for C$_{14}$H$_{17}$O$_2$N, 231; found, 232(MH$^+$).

6-[2'-Formyl-2'-(4-carbomethoxy phenyl)-ethyl]-2-desamino-2-methyl-4(3H)-oxo-quinazoline (6g)

A mixture of 3.18 g (13.77 mmol) of 4-carbomethoxy phenylacetaldehyde enamine, 3.48 g (13.77 mmol) of 2-methyl-4(3H)-oxo-6-bromomethyl quinazoline, and 800 mg (20 mmol) of MgO was stirred at 70° C. in 16 mL of DMAc for 3 hrs, during which time all the starting material had been consumed, as evidenced by TLC. The reaction mixture was extracted with 300 mL of CH$_2$Cl$_2$. The organic layer was washed repeatedly with water. After drying with anhydrous Na$_2$SO$_4$, the CH$_2$Cl$_2$ extract was evaporated to small volume. The crude reaction mixture was chromatographed on a column made of silica gel in CH$_2$Cl$_2$. Elution of the column with 2.25% MeOH/CH$_2$Cl$_2$ and evaporation of the desired fractions (TLC) gave pure 5 as a light yellow solid: Yield 2.2 g (45.6%); mp 194°–197° C.; MS(FAB$^+$), calculated for C$_{20}$H$_{18}$O$_4$N$_2$, 350; found, 351(MH$^+$).

EXAMPLE 7g

4-Carbomethoxy phenylacetaldehyde enamine

To a solution of 10.74 g (57 mmol) of 4-carbomethoxy phenylacetaldehyde in 200 mL of benzene was added 5.14 mL (61 mmol) of pyrrolidine and 9 g of MgSO$_4$ power. The reaction mixture was stirred at 25° C. for 24 hrs and filtered. The filtrate was evaporated to 40 mL and the yellow precipitate was filtered and washed with a small amount of ether. 4-Carbomethoxy phenylacetaldehyde enamine was obtained as yellow crystal. Yield 8.0 g (60.7%); mp 131°–132° C.; MS(FAB$^+$), calculated for C$_{14}$H$_{17}$O$_2$N, 231; found, 232(MH$^+$).

6-[2'-Formyl-2'-(4-carbomethoxy phenyl)-ethyl]-2-pivaloylamino-4(3H)-oxo-quinazoline A mixture of 3.53 g (15 mmol) of 4-carbomethoxy phenylacetaldehyde enamine, 5.07 g (15 mmol) of 2-pivaloylamino-4(3H)-oxo-6-(bromomethyl)-quinazoline, and 900 mg (22.5 mmol) of MgO was stirred at 80° C. in 25 mL of DMAc for 2.5 hrs, during which time all the starting material had been consumed, as evidenced by TLC. The reaction mixture was extracted with 150 mL of CH$_2$Cl$_2$. The organic layer was washed repeatedly with water. After drying with anhydrous Na$_2$SO$_4$, the CH$_2$Cl$_2$ extract was evaporated to a small volume. The crude reaction mixture was chromatographed on a column made of silica gel in CH$_2$Cl$_2$. Elution of the column with 1% MeOH/CH$_2$Cl$_2$ and evaporation of the desired fractions (TLC) gave a yellow gum: Yield 4.3 g (65.9%); MS(FAB$^+$), calculated for C$_{24}$H$_{25}$O$_5$N$_3$, 435; found, 436(MH$^+$).

6-[2'-Hydroxymethyl-2'-(4-carbomethoxy phenyl)-ethyl]-2-amino-4(3H)-oxo-quinazoline (7g)

To a solution of 1.5 g (3.45 mmol) of 2-Pivaloylamino-6-[2'-formyl-2'-(4-carbomethoxy phenyl)-ethyl]-4(3H)-oxo-quinazoline in 40 mL of MeOH was added 240 mg (6.3 mmol) of NaBH$_4$ and stirred at room temperature for 18 hrs. The pH of the solution was adjusted to 6.5 by 1.0N HCl and evaporated to small volume. The resultant residue was triturated with 10 g of ice and the precipitate thus obtained was filtered, washed with water followed by CH$_2$Cl$_2$ and dried in vacuum to obtain a light yellow solid; yield 650 mg (83%); mp 262°–263° C.; MS (FAB$^+$), calculated for C$_{19}$H$_{19}$O$_4$N$_3$, 353; found, 354 (MH$^+$).

EXAMPLE 8g

4-Carbomethoxy phenylacetaldehyde enamine

To a solution of 10.74 g (57 mmol) of 4-carbomethoxy phenylacetaldehyde in 200 mL of benzene was added 5.14 mL (61 mmol) of pyrrolidine and 9g of MgSO$_4$ power. The reaction mixture was stirred at 25° C. for 24 hrs and filtered. The filtrate was evaporated to 40 mL and the yellow precipitate was filtered and washed with a small amount of ether. 4-Carbomethoxy phenylacetaldehyde enamine was obtained as yellow crystal. Yield 8.0 g (60.7%); mp 131°–132° C.; MS(FAB$^+$), calculated for C$_{14}$H$_{17}$O$_2$N, 231; found, 232(MH$^+$).

6-[2'-Formyl-2'-(4-carbomethoxy phenyl)-ethyl]-2-desamino-2-methyl-4(3H)-oxo-quinazoline A mixture of 3.18 g (13.77 mmol) of 4-carbomethoxy phenylacetaldehyde enamine, 3.48 g (13.77 mmol) of 2-methyl-4(3H)-oxo-6-bromomethyl quinazoline, and 800 mg (20 mmol) of MgO was stirred at 70° C. in 16 mL of DMAc for 3 hrs, during which time all the starting material had been consumed, as evidenced by TLC. The reaction mixture was extracted with 300 mL of CH$_2$Cl$_2$. The organic layer was washed repeatedly with water. After drying with anhydrous Na$_2$SO$_4$, the CH$_2$Cl$_2$ extract was evaporated to small volume. The crude reaction mixture was chromatographed on a column made of silica gelin CH$_2$Cl$_2$. Elution of the column with 2.25% MeOH/CH$_2$Cl$_2$ and evaporation of the desired fractions (TLC) gave pure 7 as a light yellow solid: Yield 2.2 g (45.6%); mp 194°–197° C.; MS(FAB$^+$), calculated for C$_{20}$H$_{18}$O$_4$N$_2$, 350; found, 351 (MH$^+$).

6-[2'-Hydroxymethyl-2'-(4-carbomethoxy phenyl)-ethyl]-2-desamino-2-methyl-4(3H)-oxo-quinazoline (8g)

To a stirring solution of 1.7 g (4.84 mmol) of 5 in 150 mL of MeOH was added 185 mg (5 mmol) of NaBH$_4$. The reaction mixture was stirred at room temperature for 2.5 hrs. After adjusting the pH to 6.0 with 1.0N HCl, the reaction mixture was evaporated under reduced pressure and 50 g of ice was added. On trituration, a white solid was formed, which was filtered, washed several times with ice water followed by CH$_2$Cl$_2$. Yield 1.3 g (76.3%); mp 222°–224° C.; MS(FAB$^+$), calculated for C$_{20}$H$_{20}$O$_4$N$_2$, 352; found, 353 (MH$^+$).

In accordance with the foregoing disclosure, the following is claimed as inventive and patentable embodiments thereof:

1. Quinazoline compounds having the following formula wherein R"

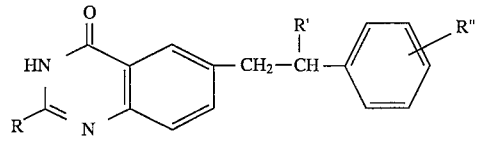

R = —NH$_2$; R' = —CHO;

selected from the group consisting of —C(=O)—OCH$_3$; —F; —CF$_3$; —NO$_2$; —NH$_2$ —Cl; —Br; —CH$_3$; —OCH$_3$; —OH; —C$_6$H$_5$; or —OC$_6$H$_5$.

2. Quinazoline compound according to claim 1 wherein R$^{11}$ is a carbomethoxy at any position in the benzene ring.

3. Quinazoline compound according to claim 1 wherein $R^{11}$ is a fluorine at any position in the benzene ring.

4. Quinazoline compound according to claim wherein $R^{11}$ is a trifluoromethyl at any position in the benzene ring.

5. Quinazoline compound according to claim 1 wherein $R^{11}$ is a nitro at any position in the benzene ring.

6. Quinazoline compound according to claim 1 wherein $R^{11}$ is a amino at any position in the benzene ring.

7. Quinazoline compound according to claim 1 wherein $R^{11}$ is a Cl at any position in the benzene ring.

8. Quinazoline compound according to claim 1 wherein $R^{11}$ is a Br at any position in the benzene ring.

9. Quinazoline compound according to claim 1 wherein $R^{11}$ is a $CH_3$ at any position in the benzene ring.

10. Quinazoline compound according to claim 1 wherein $R^{11}$ a methoxy at any position in the benzene ring.

11. Quinazoline compound according to claim 1 wherein $R^{11}$ is a hydroxy at any position in the benzene ring.

12. Quinazoline compound according to claim 1 wherein $R^{11}$ is a phenyl at any position in the benzene ring.

13. Quinazoline compound according to claim 1 wherein $R^{11}$ is a phenoxy at any position in the benzene ring.

14. Quinazoline compounds having the following formula

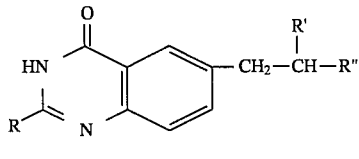

$R = -NH_2; \quad R' = -CHO;$

Wherein $R^{11}$ is selected from a group of ring systems consisting of pyridyl; naphthyl, thienyl, furanyl, quinolyl and adamantyl.

15. Quinazoline compound according to claim 14 wherein $R^{11}$ is a pyridyl.

16. Quinazoline compound according to claim 14 wherein $R^{11}$ is a naphthyl.

17. Quinazoline compound according to claim 14 wherein $R^{11}$ is a theonyl.

18. Quinazoline compound according to claim 14 wherein $R^{11}$ is a furanyl.

19. Quinazoline compound according to claim 14 wherein $R^{11}$ is a quinolyl.

20. Quinazoline compound according to claim 14 wherein $R^{11}$ is an adamantyl.

21. Quinazoline compound having the following formula

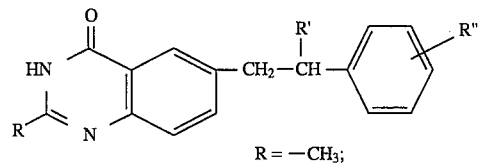

$R = -CH_3;$

Wherein $R^1$ is a formyl or a hydroxymethyl and $R^{11}$ is selected from the group consisting of —F, —$CF_3$; —$NO_2$; $NH_2$; Cl; Br; —$CH_3$; —$COOCH_3$; —$OCH_3$; —OH; —$C_6H_5$ or —$OC_6H_5$ at any position in the benzene ring.

22. 10-Formyl-10-deazaquinazoline compound (1) having the following formula

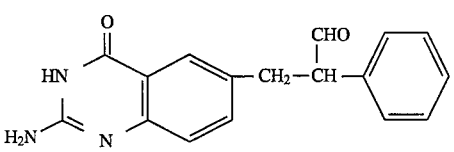

23. 10-Hydroxymethyl-10-deazaquinazoline compound (2) having the following formula

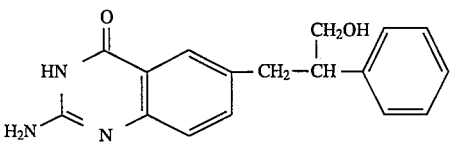

24. 10-Formyl-10-deaza-2-desamino-2-methylquinazoline compound (3) having the following formula

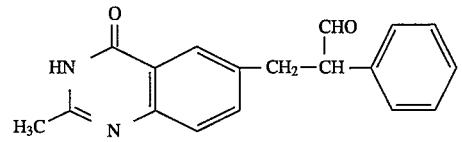

25. 10-Hydroxymethyl-10-deaza-2-desamino-2-methylquinazoline compound (4) having the following formula

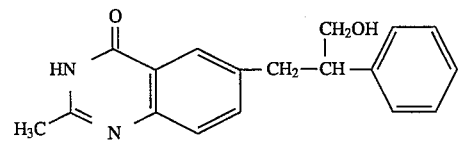

* * * * *